United States Patent [19]
Tanemura et al.

[11] Patent Number: 4,698,364
[45] Date of Patent: Oct. 6, 1987

[54] BENZOIC ACID DERIVATIVES

[75] Inventors: Mitsuru Tanemura; Isao Matsunaga, both of Tokyo; Masami Saitou, Kanagawa, all of Japan

[73] Assignee: Chugai Seiyaku Kabushiki Kaisha, Tokyo, Japan

[21] Appl. No.: 788,972

[22] Filed: Oct. 18, 1985

[30] Foreign Application Priority Data

Oct. 19, 1984 [JP] Japan ................................ 59-218518
Oct. 19, 1984 [JP] Japan ................................ 59-218519

[51] Int. Cl.$^4$ .................. A61K 31/10; A61K 31/165; C07C 149/40; C07C 149/41
[52] U.S. Cl. .................................... 514/563; 514/576; 514/616; 560/11; 560/12; 560/18; 562/429; 562/430; 562/431; 562/432; 564/154
[58] Field of Search .............................. 560/11, 12, 18; 562/429, 430, 431, 432; 514/563, 576, 616; 564/154

[56] References Cited
U.S. PATENT DOCUMENTS

| | | | |
|---|---|---|---|
| 1,769,423 | 7/1930 | Eder ..................................... | 562/432 |
| 1,841,636 | 1/1931 | Saunders et al. ............... | 562/432 X |
| 3,385,863 | 5/1968 | Wick et al. ....................... | 562/432 X |
| 3,514,480 | 5/1970 | Fields ............................... | 562/432 X |
| 3,657,431 | 4/1972 | Shen et al. ....................... | 562/432 X |

OTHER PUBLICATIONS

Chemical Abstracts, vol. 54, No. 10, 5/25/60, col. 9815, abstract c, Columbus, Ohio US, F. Gialdi et al "2,2'-Dicarbamidodiphenyl Sulfides and Sulfones", & Farmaco (Pavia) ed. Sci.14 830–44 (1959).
Tetrahedron, vol. 35, 1979, pp. 1869-1874, Pergmon Press Ltd., Oxford BG; I. Kapovits et al "Diaryldiacyloxyspirosulfuranes.I Halogenating Agents" * Formulas 2a–2c,2e,2j–2k, p. 1872, right-hand col. p. 1873.
Tetrahedron, vol. 35, 1979, pp. 1875-1881, Pergamon Press Ltd., Oxford GB; I. Kapovits et al: "Diaryldiacyloxyspirosulfuranes.I.I Syntheses from Sulfoxides and Hydrolysis" * Formulas 2a–2c, 2e,2j–2k.
Journal of the American Chemical Society, vol. 100, No. 3, Feb. 1st 1978, pp. 953–962, American Chemical Society, Easton US, L. J. Adzima et al: "Synthesis, Reactions, and Crystal and Molecular Structure . . . ".
Journal of the Chemical Society, Perkin Transactions 1, 1979, pp. 799-802, J. Grimshaw et al: "Electrochemical Reactions, Part 22, Intramolecular Trapping of Radical Intermediates in the Reduction of Arylsulphones".

Primary Examiner—Werren B. Lone
Assistant Examiner—Vera C. Clarke
Attorney, Agent, or Firm—Browdy and Neimark

[57] ABSTRACT

Benzoic acid derivatives of the formula:

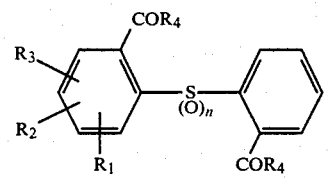

wherein n is an integer of 0 to 2; $R_1$ to $R_3$ which may be the same or different each represents a hydrogen atom, a halogen atom, a lower alkyl group, a lower alkoxy group or nitro group; $R_4$ is a hydroxyl group or the group —NHZ (Z is hydrogen atom or a lower alkyl group), or an alkali metal salts thereof are useful as an infection control agent.

These derivatives excepting compounds of the formula above wherein n is 0 or 1; any one of $R_1$ to $R_3$ is 5-chloro, 5-methoxy or 5-nitro and the remainder is a hydrogen atom; and $R_4$ is a hydroxyl group; and compounds of the formula wherein n is 0 or 1; two of $R_1$ to $R_3$ are 3,5-dichloro or 3,5-dinitro and the remainder is a hydrogen atom; and $R_4$ is a hydroxy group) are novel, and they were first prepared in this invention.

9 Claims, No Drawings

BENZOIC ACID DERIVATIVES

BACKGROUND OF THE INVENTION

The present invention relates to a benzoic acid derivative of the formula (I):

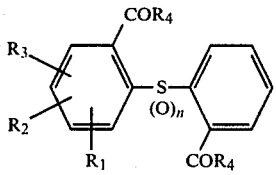

wherein n is an integer of 0 to 2; $R_1$ to $R_3$ which may be the same or different each represents a hydrogen atom, a halogen atom, a lower alkyl group (i.e. $C_1$-$C_5$), a lower alkoxy group (i.e. ($C_1$-$C_5$) or a nitro group; $R_4$ is a hydroxyl group or the group —NHZ (Z is a hydrogen atom or a lower alkyl group (i.e. $C_1$-$C_5$) or an alkali metal salt thereof.

The benzoic acid derivative of the present invention is useful as an infection control agent.

Among the benzoic acid derivatives of the formula (I), the compounds wherein n is 0 or 1; any one of $R_1$ to $R_3$ is 5-chloro, 5-methoxy, or 5-nitro and the remainder is hydrogen; and $R_4$ is a hydroxyl group; and the compounds wherein n is 0 or 1; and two of $R_1$ to $R_3$ are 3,5-dichloro or 3,5-dinitro and the remainder is hydrogen; and $R_4$ is a hydroxyl group are reported together with their preparation in Tetrahedron Vol. 35, pp. 1869-1881 (1979). However, this reference does not refer to any pharmacological activity of these compounds.

It is known that cytoskeletal proteins function as one of the structure proteins in cytoplasm. The cytoskeletal proteins are classified as microtubules, intermediate filaments and microfibers depending on the diameter size. These cytoskeletal proteins are believed to control, on the basis of their contracting ability, the motility of cells, their migration, the change and retention of their morphology, secretion, phagocytosis, adhesion and the transfer of the receptor on the cell membrane. Furthermore, evidence is being accumulated to suggest the association of cytoskeletal proteins with the growth and differentiation of cells.

The present inventors have obtained 2,2'-thiodibenzoic acid derivatives [i.e., compounds of forumla (I) wherein n=0] by reacting 2-halogenobenzoic acid derivatives of the formula:

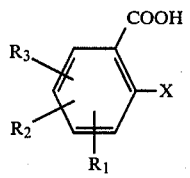

wherein $R_1$ to $R_3$ have the same meanings as defined above; and X is a halogen atom with thiosalicylic acid.

Examples of the starting halogenobenzoic acid derivatives include 2-bromo-3,4,5-trimethoxygenzoic acis, 2-bromo-4,5-dimethoxybenzoic acid, 2,4-dichlorobenzoic acid, 2-iodo-3-methyl-4-chlorobenzoic acid, 2-iodo-4,5-dimethylbenzoic acid, 2-iodo-4,6-dimethylbenzoic acid, 2-iodo-3,4-dimethylbenzoic acid, 2-iodo-3,6-dimethylbenzoic acid, 2-iodo-3,5-dimethylbenzoic acid, 2-iodo-5,6-dimethylbenzoic acid, 2-bromo-4-t-butylbenzoic acid, 2-iodo-5-n-butylbenzoic acid, 2-iodo-5-n-propylbenzoic acid, 2-iodo-5-ethylbenzoic acid, 2-iodo-5-methylbenzoic acid, 2-iodo-3-isopropylbenzoic acid, 2-iodo-3-ethylbenzoic acid, 2-iodo-3-methylbenzoic acid, 2-chloro-4-nitrobenzoic acid, 2-chloro-5-nitrobenzoic acid and 2-chloro-3,5-dinitrobenzoic acid.

The reaction between the 2-halogenobenzoic acid derivatives and thiosalicylic acid is performed at 90° C or higher in the presence of a solvent using an alkali and a metal catalyst. Generally, the reaction is carried out at 100–200° C. for 2–10 hours, and the preferred conditions are 110–130° C and 3–5 hours.

Suitable solvents are nitrobenzene, benzyl alcohol, dimethylformamide, xylene, and a mixture of toluene and dimethyformamide.

For the purposes of the present invention, thiosalicylic acid may be used in excess of the 2-halogenobenzoic acid derivative, and the preferred amount ranges from 1.1 to 1.2 moles per mole of the 2-halogenobenzoic acid. Suitable alkalis include anhydrous potassium carbonate and anhydrous sodium carbonate. Suitable metal catalysts include a metallic copper powder, and metal compounds such as cuprous chloride, cupric chloride, curpous bromide, cupric bromide and curpic acetate.

The 2,2'-thiodibenzoic acid derivative may be converted by a general method to the corresponding alkali metal salt such as sodium or potassiuim salt.

The 2,2'-thiodibenzoic acid derivative [compound of formula (I) wherein n=0] may be oxidized with hydrogen peroxide in formic acid or acetic acid at 25° C. or higher so as to obtain 2,2'-sulfonyldibenzoic acid derivative [compound of formula (I) wherein n=2]. The 2,2'-sulfonyldibenzoic acid derivative may be converted by a general method to the corresponding alkali metal salt such as sodium or potassium salt.

The 2,2'-thiodibenzoic acid derivative [compound of formula (I) wherein n=0] may be converted to an ester derivative [a novel compound of formula (I) wherin n=0 and $R_4$=a lower alkoxy group], which is then oxidized with a peracid to obtain a 2,2'-sulfinyldibenzoic acid diester derivative [a novel compound of formula (I) wherein n=1 and $R_4$ =a lower alkoxy group]. The novel compound may be hydrolyzed to obtain a 2,2'-sulfinyldibenzoic acid [compound of formula (I) wherein n=1, $R_4$=OH. The 2,2'-sulfinyldibenzoic acid derivative may be converted to the corresponding alkali metal salt such as sodium or potassium salt by a general method.

Amide derivatives of formula (I) wherein n=0, 1 or 2 and $R_4$ =NHZ (Z=H or a lower alkyl group) may be synthesized from 2,2'-thiodibenzoic acid derivatives, 2,2'-sulfinyldibenzoic acid derivatives by a general method.

The present invention has been accomplished on the basis of the finding of the inventors that the compounds of formula (I) promote the migrating and phagocytotic abilities of macrophages in association with the cytoskeletal proteins.

The compounds of formula (I) can be formulated by any desirable conventional method with a pharmaceutically acceptable carrier.

For oral administration, the compound of this invention can be formulated into a solid preparation such as a tablets, pills, granules, powder, capsules, or the like, or a liquid preparation such as solution, suspension, emulsion or the like. When the preparation is used for parenteral administration, the preparation is formulated into a suppository, injection, an intravenous drip infusion or the like. When the compound of this invention is formulated into tablets, pills, granules, powder or capsules, pharmaceutical carriers such as starch, sucrose, crystalline cellulose, kaolin, calcium carbonate, talc, magnesium carbonate and the like are preferably used. For preparation of an injection, it is preferred that the compound is dissolved in distilled water or an aqueous solution of a salt such as sodium chloride. For preparation of an intravenous drip infusion, the compound is dissolved in a suitable fluid therapy such as a physiological saline, a glucose-sodium chloride solution or the like. For a suppository, cacao butter, laurin, glycerogelatin, macrogol are preferably used as a base.

The amount of the compound in a formulated preparation is selected so as to be appropriately administered depending on the age and condition of individual patient being treated.

The compound of this invention is preferably administered orally in a daily dose of from 10 mg to 2000 mg/day and parenterally in a daily dose of from 50 mg to 1000 mg/day.

The compounds of formula (I) of the present invention will exhibit an excellent ability to protect animals with reduced immunological functions from contracting infections. The present invention is hereunder described in greater detail by references to working examples and experiments.

EXAMPLE 1

A mixture of 2,4-dichlorobenzoic acid (7.64 g), thiosalicylic acid (7.16 g), anhydrous potassium carbonate (22 g), and copper powder (300 mg) was suspended in benzyl alcohol and this suspension was heated under $N_2$ atmosphere at 110–120° C. for 3 hours. After cooling, 10% aqueous potassium hydroxide solution (120 ml) was added and extracted with ether. The aqueous layer was filtered and acidified with 6N HCl. The resulting precipitated product was isolated by filtration. Recrystallization from aqueous methanol gave 4-chloro-2,2'-thiodibenzoic acid (compound No. 1) in an amount of 8.56 g (yield: 70%). m.p. 241–242° C.

Elemental analysis for $C_{14}H_9ClO_4S$:
Calculated(%): C, 54.46, H, 2.94, Cl, 11.48
Found (%): C, 54.32, H, 2.95, Cl, 11.50.

EXAMPLES 2 to 24

Compound Nos. 2–24 as identified in Table 1 were produced by repeating the procedures of Example 1.

TABLE 1

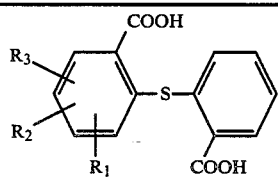

| Compound No. | $R_1$ | $R_2$ | $R_3$ | m.p. (°C.) |
|---|---|---|---|---|
| 2 | 3-$CH_3$ | H | H | 258–259 |
| 3 | 3-$C_2H_5$ | H | H | 218–219 |
| 4 | 3-$i$-$C_3H_7$ | H | H | 232–235 |
| 5 | 5-$CH_3$ | H | H | 194–196 |
| 6 | 5-$C_2H_5$ | H | H | 209–210 |
| 7 | 5-$n$-$C_3H_7$ | H | H | 191–193 |
| 8 | 5-$n$-$C_4H_9$ | H | H | 183–184 |

TABLE 1-continued

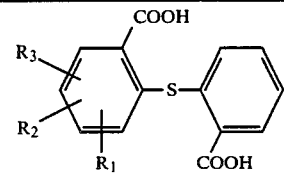

| Compound No. | $R_1$ | $R_2$ | $R_3$ | m.p. (°C.) |
|---|---|---|---|---|
| 9 | 4-F | H | H | 247–248 |
| 10 | 3-$CH_3$ | 4-Cl | H | 280< |
| 11 | 3-$CH_3$ | 5-$CH_3$ | H | 284–286 |
| 12 | 5-$CH_3$ | 6-$CH_3$ | H | 239–240 |
| 13 | 4-$CH_3$ | 5-$CH_3$ | H | 240–241 |
| 14 | 4-$CH_3$ | 6-$CH_3$ | H | 231–232 |
| 15 | 3-$CH_3$ | 6-$CH_3$ | H | 252–254 |
| 16 | 4-$OCH_3$ | 5-$OCH_3$ | H | 249–250 |
| 17 | 3-$OCH_3$ | 4-$OCH_3$ | 5-$OCH_3$ | 230–231 |
| 18 | 3-$CH_3$ | 4-$CH_3$ | H | 279–282 |
| 19 | 4-$t$-$C_4H_9$ | H | H | 221–223 |
| 20 | 5-$NO_2$ | H | H | 267–268 |
| 21 | 4-$NO_2$ | H | H | 290–291 |
| 22 | 3-$NO_2$ | 5-$NO_2$ | H | 300< |
| 23 | 5-Cl | H | H | 247–250 |
| 24 | 5-$OCH_3$ | H | H | 225–227 |

EXAMPLE 25

Dimethyl 4-chloro-2,2'-thiodibenzoate (6.72 g) was dissolved in methylene chloride. To the solution was added m-chloroperbenzoic acid (4 g) and the solution was stirred at room temperature for 6 hours. The reaction mixture was poured into a 10% aqueous sodium hydroxide solution and extracted with methylene chloride. The methylene chloride extract was washed with saturated aqueous sodium chloride, dried over magnesium sulfate, filtered, and the filtrate was evaporated to give a product. The product was suspended into a 20% aqueous sodium hydroxide solution and heated at 60° C. for 3 hours. After cooling, the solution was acidified with 6N HCl to give a precipitate. Recrystallization from aqueous methanol gave 4-chloro-2,2'-sulfinyldibenzoic acid (compound No. 25) in an amount of 4.5 g (yield: 70%). m.p. 279–281° C.

Elemental analysis for $C_{14}H_9ClO_5S$:
Calculated (%): C, 51.78, H, 2.79, Cl, 10.92
Found (%): C, 51.85, H, 2.60, Cl, 11.13.

EXAMPLES 26 to 34

Compound Nos. 26–34 as identified in Table 2 were produced by repeating the procedures of Example 25.

TABLE 2

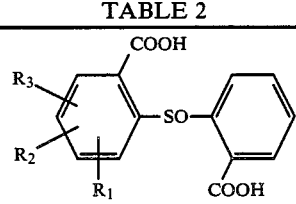

| Compound No. | $R_1$ | $R_2$ | $R_3$ | m.p. (°C.) |
|---|---|---|---|---|
| 26 | 3-$OCH_3$ | 4-$OCH_3$ | 5-$OCH_3$ | 172–174 |
| 27 | 4-$t$-$C_4H_9$ | H | H | 232–233 |
| 28 | 4-$NO_2$ | H | H | 273–274 |
| 29 | 5-$NO_2$ | H | H | 270–271 |
| 30 | 3-$NO_2$ | 5-$NO_2$ | H | 250–252 |
| 31 | 4-$OCH_3$ | 5-$OCH_3$ | H | 230–232 |
| 32 | 5-$t$-$C_4H_9$ | H | H | 157–158 |

TABLE 2-continued

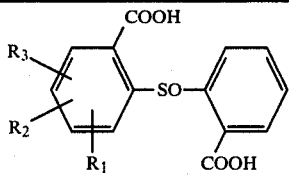

| Compound No. | $R_1$ | $R_2$ | $R_3$ | m.p. (°C.) |
|---|---|---|---|---|
| 33 | 5-$C_2H_5$ | H | H | 141–142 |
| 34 | 5-Cl | H | H | 251–256 |

EXAMPLE 35

Eight grams of 4-chloro 2,2'-thiodibenzoic acid was suspended in acetic acid (60 ml). To the suspension, 35% aqueous $H_2O_2$ (21 ml) was added and stirred at room temperature for 3 hours, followed by heating at 50–60° C. for 3 hours. The reaction mixture was poured into ice water and the precipitated product was isolated by filtration. Recrystallization from aqueous methanol gave 4chloro-2,2'-sulfonyldibenzoic acid (compound No. 35) in an amount of 6.2 g (yield: 70%). m.p. 276–277° C.

Elemental analysis for $C_{14}H_9ClO_6S$:
Calculated (%): C, 49.35, H, 2.66, Cl, 10.40
Found (%): C, 49.52, H, 2.89, Cl, 10.69

EXAMPLES 36 to 57

Compound Nos. 36 to 57 as identified in Table 3 were produced by repeating the procedures of Example 35.

TABLE 3

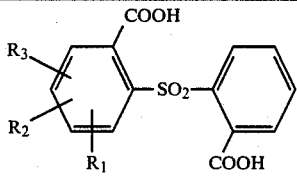

| Compound No. | $R_1$ | $R_2$ | $R_3$ | m.p. (°C.) |
|---|---|---|---|---|
| 36 | 3-$CH_3$ | H | H | 251–252 |
| 37 | 3-$C_2H_5$ | H | H | 240–241 |
| 38 | 3-i-$C_3H_7$ | H | H | 256–257 |
| 39 | 5-$CH_3$ | H | H | 254–255 |
| 40 | 5-$C_2H_5$ | H | H | 195–196 |
| 41 | 5-n-$C_3H_7$ | H | H | 145–146 |
| 42 | 5-n-$C_4H_9$ | H | H | 138–139 |
| 43 | 5-$OCH_3$ | H | H | 196–197 |
| 44 | 4-F | H | H | 259–260 |
| 45 | 3-$CH_3$ | 4-Cl | H | 247–248 |
| 46 | 3-$CH_3$ | 5-$CH_3$ | H | 252–253 |
| 47 | 5-$CH_3$ | 6-$CH_3$ | H | 211–212 |
| 48 | 4-$CH_3$ | 5-$CH_3$ | H | 252–253 |
| 49 | 4-$CH_3$ | 6-$CH_3$ | H | 242–243 |
| 50 | 3-$CH_3$ | 6-$CH_3$ | H | 286–287 |
| 51 | 4-$OCH_3$ | 5-$OCH_3$ | H | 254–255 |
| 52 | 3-$OCH_3$ | 4-$OCH_3$ | 5-$OCH_3$ | 210–212 |
| 53 | 5-Cl | H | H | 278–279 |
| 54 | 4-t-$C_4H_9$ | H | H | 241–243 |
| 55 | 4-$NO_2$ | H | H | 257–258 |
| 56 | 5-$NO_2$ | H | H | 241–242 |
| 57 | 3-$NO_2$ | 5-$NO_2$ | H | 256–257 |

EXAMPLE 58

A suspension of 3-ethyl-2,2'-thiodibenzoic acid (3.3 g) in dry benzene (30 ml) was added to thionyl chloride (15 ml) and the suspension was stirred under reflux for 3 hours. The reaction mixture was then concentrated under reduced pressure to give a precipitate. The precipitate was dissolved in tetrahydrofuran (30 ml), and to the solution, 30 ml of 40% aqueous methylamine was added dropwise under cooling with ice. After addition, the reaction mixture was stirred overnight at room temperature. After concentration, a 10% aqueous sodium hydroxide solution was added to the concentrate and the precipitated product was isolated by filtration. Recrystallization from benzene–n-hexane gave an amide derivative (compound No. 58) in an amount of 2 g (yield: 56%) m.p. 191–192° C.

Elemental analysis for $C_{18}H_{20}O_2N_2S$:
Calculated (%): C, 65.83, H, 6.14
Found (%): C, 65.42, H, 6.13

EXAMPLES 59 to 69

Compound Nos. 59–69 as identified in Table 4 were produced by repeating the procedures of Example 58.

TABLE 4

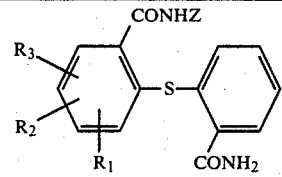

| Compound No. | $R_1$ | $R_2$ | $R_3$ | Z | m.p. (°C.) |
|---|---|---|---|---|---|
| 59 | 5-n-$C_3H_7$ | H | H | $CH_3$ | 166–167 |
| 60 | 4-$CH_3$ | 6-$CH_3$ | H | $CH_3$ | 200–202 |
| 61 | 5-$C_2H_5$ | H | H | $CH_3$ | 150–152 |
| 62 | 4-Cl | H | H | $CH_3$ | 212–214 |
| 63 | 5-$CH_3$ | H | H | $CH_3$ | 176–177 |
| 64 | 3-$CH_3$ | H | H | $CH_3$ | 173–175 |
| 65 | 5-n-$C_4H_9$ | H | H | $CH_3$ | 120–123 |
| 66 | 3-$CH_3$ | 5-$CH_3$ | H | $CH_3$ | 199–200 |
| 67 | 4-Cl | H | H | $C_2H_5$ | 166–167 |
| 68 | 3-$CH_3$ | 6-$CH_3$ | H | $C_2H_5$ | 192–193 |
| 69 | 4-Cl | H | H | i-$C_3H_7$ | 180–181 |

EXAMPLE 70

N,N'-Diethyl-4-chloro-2,2'-thiodibenzoic acid diamide (1.6 g) was dissolved in dry methylene chloride (60 ml). To the solution, m-chloroperbenzoic acid (0.8 g) was added under cooling with ice. The solution was stirred at room temperature for 1.5 hours. The solution was washed with saturated aqueous sodium hydrogencarbonate and with saturated aqueous sodium chloride, and dried over magnesium sulfate. The solvent was evaporated under reduced pressure to give a crude product. Recrystallization from benzene–n-hexane gave N,N'-diethyl-4-chloro-2,2'-sulfinyldibenzoic acid diamide (compound No. 70) in an amount of 1.5 g. m.p. 200–202° C.

EXAMPLE 71

Five grams of 4-chloro-2,2'-sulfinyldibenzoic acid was suspended in dry benzene (50 ml). The the suspension was added thionyl chloride (50ml), and the suspension was stirred under reflux for 3 hours. The reaction mixture was concentrated under reduced pressure to give an acid chloride. The acid chloride was dissloved in tetrahydrofuran (50ml) and to the solution was added dropwise 40% of aqueous methylamine (50 ml) under cooling with ice. After addition, the solution was concentrated under reduced pressure, and to the concentrate, a 5% aqueous sodium hydroxide solution was added. The precipitated product was isolated by filtration. Recrystallization from benzene–n-hexane gave 3.4 g of N,N'-dimethyl-4-chloro-2,2'-sulfinyldibenzoic acid diamide (compound No. 71). m.p. 203–205° C.

EXAMPLE 72 By repeating the procedures of Example 71, N,N'-dimethyl-5-n-butyl-2, 2'-sulfinyldibenzoic acid diamide (compound No. 72) having a melting point of 132–133° C was obtained.

EXAMPLE 73

Four grams of 4-chloro-2,2'-sulfonyldibenzoic acid was suspended in dry benzene (50 ml). To the suspension, thionyl chloride (20 ml) was added and the suspension was stirred under reflux for 3 hours. The solvent was concentrated under reduced pressure to give an acid chloride. The acid chloride was dissolved in terahydrofuran (50 ml), and to the solution, 40% aqueous methylamine (50 ml) was added dropwise under cooling with ice. After addition, the solution was stirred overnight at room temperature. The reaction mixture was concentrated under reduced pressure, and to the concentrate, a 5% aqueous sodium hydroxide solution was added. The precipitated product was isolated by filtration. Recrystallization from benzene–n-hexane gave 2.1 g of N,N'-dimethyl-4-chloro-2,2'-sulfonyldibenzoic acid diamide (compound No. 73). m.p. 221–222° C. This compound may also be produced by the following procedure. In acetic acid (30 ml), N,N'-dimethyl-4-chloro-2,2'-thiodibenzoic acid diamide(3.3 g) was suspended. To the suspension, 35% aqueous $H_2O_2$ was added, and the suspension was stirred at room temperature for 3 hours, followed by heating at 50–60° C. for 3 hours under stirring. The reaction mixture was poured into ice water and was extracted with ethyl acetate. The ethyl acetate extract was washed with saturated aqueous sodium hydrogencarbonate, and with saturated aqueous sodium chloride, dried over magnesium sulfate, filtered and the filtrate was evaporated to give a crude product. Recrystallization from benzene-–n-hexane gave 2.8 g of N,N'-dimethyl-4-chloro-2,2'-sulfonyldibenzoic acid diamide, m.p. 221–222° C.

EXAMPLE 74

By repeating the procedures of Example 73, N,N'-dimethyl-5-nitro-2, 2'-sulfonyldibenzoic acid diamide (compound No. 74) having a melting point of 221–223° C was obtained.

EXAMPLE 75

In distilled water (50 ml), 7.12 g of 4-chloro-2,2'-sulfonyldibenzoic acid was suspended. To the suspension, 20 ml of a 2N aqueous sodiium hydroxide solution was added and the suspension was heated at 70° C. for 3–4 hours. After cooling, the solution was filtered and evaporated under reduced pressure. The precipitated product was isolated and dried under vacuum to give a disodium salt of 4-chloro-2,2'-sulfonyldibenzoic acid in a quantitiative yield. In a similar manner, disodiium salts of compound Nos. 1 to 57 could be synthesized.

EXPERIMENT 1

Resistance to Injection in S-180 Cancer Bearing Mice

Groups of ICR mice (22–25 g, ♂ and ♀), each group consisting of ten mice, were subcutaneously injected in the back with 0.1 ml of suspension of $1 \times 10^6$ S-180 cells. During the period of the 11th to 13th days of injection, selected compounds of the present invention were orally administered to the mice in doses of 120 mg/kg/day. On the 14th day of injection, $1 \times 10^8$ Salmonella typhimurium cells were injected into the animals through the tail vein and the length of their survival was recorded. The results are shown in Table 6.

TABLE 6

| Compound No. | Survival days (means ± S.D.) |
|---|---|
| Normal | 8.9 ± 1.0 |
| Control | 2.9 ± 0.9 |
| Compound 1 (Na salt) | 4.0 ± 1.2 |
| 12 (Na salt) | 3.8 ± 1.1 |
| 23 (Na salt) | 3.9 ± 1.1* |
| 24 (Na salt) | 4.8 ± 1.3* |
| 34 (Na salt) | 5.1 ± 1.3* |
| 35 (Na salt) | 7.4 ± 1.3* |
| 37 (Na salt) | 6.6 ± 1.2* |

*$P < 0.05$

EXPERIMENT 2

Migration Activity of Peritoneal Macrophages in EL 4 Cancer Bearing C57BL Mice

C57BL mice were injected subcutaneously in the back with $1 \times 10^6$ mouse leukemic cells EL4. During the period of the 1st to 4th day of injection, selected compounds of the present invention were orally administered to the mice in doses of 2 mg/mouse/day. On the fifth day of injection, peritoneal cells were collected from each animal and suspended in Culture Solution I (indicated below) at a concentration of $2 \times 10^6$ cells/ml. A Boiden Chamber (BioRad Laboratories, USA) equipped with a millipore filter (5 micron in pore size) was set in a $Co_2$ incubator; 0.2 ml of Culture Solution II (indicated below) was placed in the lower part of the filter while 0.2 ml of the previously prepared peritoneal cell suspension was put in the upper part of the filter. After incubation at 37° C. for 90 minutes, the filter was removed from the chamber, fixed with methanol and Giemsastained. The number of cells that passed through the filter within one visual field under a microscope (400 x) was counted, and the results are shown in Tables 7 and 8 below. Culture Solution I: RPMI-1640 culture solution (Nissui Pharmaceutical Co., Ltd.) containing
10% fetal calf serum, FCS (Microbiological
Laboratories, USA), 50 units/
ml of penicillin G and 50 μg/ml of
streptomycin. Culture Solutin II: RPMI-1640 culture solution containing
10% zymosan-activated human serum, ZAS.

TABLE 7

| Compound No. | Migration activity relative to the normal value (%) (mean ± S.D.) |
|---|---|
| Normal (no compound administered) | 100 ± 12.2 (28.8 ± 3.5 cells/field) |
| Bearing EL4 cancer | |
| no compound administered | 20.9 ± 4.3 |
| compound 1 (Na salt) | 60.8 ± 17.7 |
| 12 (Na salt) | 60.0 ± 11.7 |
| 24 (Na salt) | 67.4 ± 7.1 |
| 35 (Na salt) | 104.1 ± 12.8 |
| 37 (Na salt) | 90.6 ± 18.0 |

TABLE 8

| Compound No. | Migration activity relative to the normal value (%) (mean ± S.D.) |
| --- | --- |
| Normal (no compound administered) | 100 ± 10.1 (19.5 ± 1.96 cells/field) |
| Bearing EL4 cancer | |
| no compound administered | 12 ± 5.0 |
| compound 36 (Na salt) | 99 ± 48 |
| 38 (Na salt) | 90 ± 22 |
| 39 (Na salt) | 54 ± 12 |
| 40 (Na salt) | 77 ± 14 |
| 41 (Na salt) | 87 ± 24 |
| 43 (Na salt) | 129 ± 56 |
| 45 (Na salt) | 103 ± 21 |
| 47 (Na salt) | 109 ± 12 |
| 52 (Na salt) | 124 ± 9.1 |
| 60 | 60 ± 11 |

What is claimed is:
1. A compound of the formula:

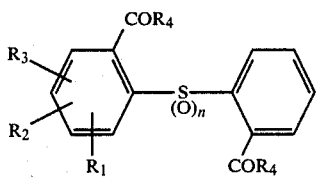

wherein n is an integer of 0 to 2; $R_1$ and $R_3$ which may be the same or different each represents a hydrogen atom, a halogen aton, a lower alkyl group, a lower alkoxy group or a nitro group; $R_4$ is a hydroxyl group or the group —NHZ, Z being a hydrogen atom or a lower alkyl group, excepting both the case where n is 0 or 1, any one of $R_1$ to $R_3$ is 5-chloro, 5-methoxy or 5-nitro and the remainder is a hydrogen atom, and $R_4$ is a hydroxyl group, and the case where n is 0 or 1, any two substituents of $R_1$ to $R_3$ are 3,5-dichloro or 3,5-dinitro and the remainder is a hydrogen atom, and $R_4$ is a hydroxyl group or an alkali metal salt hereof.

2. A compound of the formula:

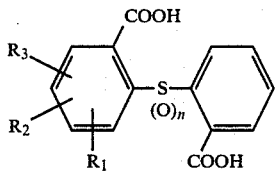

wherein n is an integer of 0 to 2; $R_1$ to $R_3$ which may be the same or different each represents a hydrogen atom, a halogen atom, a lower alkyl group, a lower alkoxy group or a nitro group, excepting both the case where n is 0 or 1, any one of $R_1$ to $R_3$ is 5-chloro, 5-methoxy or 5-nitro, adn the remainder is a hydrogen atom, and the case where n is 0 or 1, two substituents of $R_1$ to $R_3$ are 3,5-dichloro or 3, 5-dinitro and the remainder is a hydrogen atom or an alkali metal sal thereof.

3. A compound of the formula:

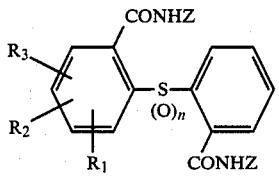

wherein n is an integer of 0 to 2; Z is a hydrogen atom or a lower alkyl group; $R_1$ to $R_3$ which may be the same or different each represents a hydrogen atom, a halogen atom, a lower alkyl group, a lower alkoxy group or a nitro group.

4. A process for producing a compound of the formula:

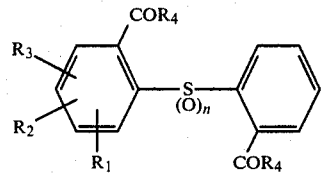

wherein n is an integer of 0 to 2; $R_1$ to $R_3$ which may be the same or different each represents a hydrogen atom, a halogen atom, a lower alkyl group, a lower alkoxy group or a nitro group; $R_4$ is a hydroxyl group or the group —NHZ, Z being a hydrogen atom or a lower alkyl group, excepting both the case where n is 0 or 1, any one of $R_1$ to $R_3$ is 5-chloro, 5-methoxy or 5-nitro and the remainder is a hydrogen atom, and $R_4$ is a hydroxyl group, and the case where n is 0 or 1, two substituents of $R_1$ to $R_3$ are 3,5-dichloro or 3,5-dinitro and the remainder is a hydrogen atom, and $R_4$ is a hydroxyl group or an alkali metal salt thereof by reacting a 2-halogenobenzoic acid derivative of the formula:

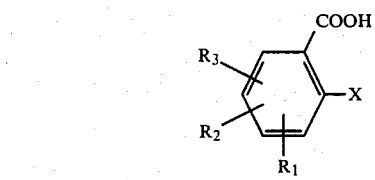

wherein $R_1$ to $R_3$ are the same as defined above; and X is a halogen atom, with thiosalicylic acid, oxidizing, amidating, esterifying or hydrolyzing the reaction product as required, and optionally converting the so treated product to an alkali metal salt.

5. A process according to claim 4 wherein the reaction between the 2-halogenobenzoic acid derivative and thiosalicylic acid is performed in an organic solvent at 100–200° C. for 2–10 hours using an alkali and a copper catalyst.

6. A process according to claim 5 wherin said organic solvent is selected from the group consisting of nitrobenzene, benzyl alcohol, dimethylformamide xylene, and a mixed solvent of toluene and dimethylformamide.

7. A process according to claim 5 wherein said alkali is anhydrous potassium carbonate or anhydrous sodium carbnate.

8. A process according to claim 5 wherein said copper catalyst is selected from the group consisting of cuprous chloride, cupric chloride, cuprous bromide, cupric bromide and cupric acetate.

9. A pharmaceutical compositon for controlling infectious diseases, which comprises a pharmaceutically acceptable carrier an an effective amount of a compound of the formula:

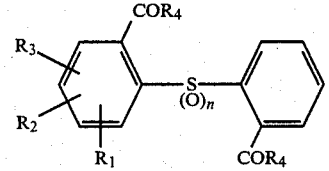

wherein n is an integer of 0 to 2; $R_1$ to $R_3$ which may be the same or different each represents a hydrogen atom, a halogen atom, a lower alkyl group, a lower alkoxy group or a nitro group; and $R_4$ is a hydroxyl group or the group —NHZ, Z being a hydrogen atom or a lower alkyl group, or an alkali metal salt thereof.

* * * * *